United States Patent
Beldon et al.

(10) Patent No.: US 12,402,793 B2
(45) Date of Patent: Sep. 2, 2025

(54) NEAR-INFRARED IMAGING SYSTEM FOR IDENTIFYING A TARGET FEATURE IN AN OBJECT

(71) Applicant: CORTIRIO LIMITED, Sedgefield (GB)

(72) Inventors: Patrick Beldon, Sedgefield (GB); Paul Macey, Sedgefield (GB)

(73) Assignee: Cortirio Limited, Sedgefield (GB)

( * ) Notice: Subject to any disclaimer, the term of this patent is extended or adjusted under 35 U.S.C. 154(b) by 101 days.

(21) Appl. No.: 18/275,717

(22) PCT Filed: Feb. 3, 2022

(86) PCT No.: PCT/GB2022/050283
§ 371 (c)(1),
(2) Date: Aug. 3, 2023

(87) PCT Pub. No.: WO2022/167801
PCT Pub. Date: Aug. 11, 2022

(65) Prior Publication Data
US 2024/0081651 A1 Mar. 14, 2024

(30) Foreign Application Priority Data
Feb. 4, 2021 (GB) .................. 2101565

(51) Int. Cl.
*A61B 5/00* (2006.01)
*A61B 8/08* (2006.01)

(52) U.S. Cl.
CPC .......... *A61B 5/0075* (2013.01); *A61B 5/0073* (2013.01); *A61B 8/085* (2013.01)

(58) Field of Classification Search
CPC ...... A61B 5/0075; A61B 5/0073; A61B 8/085
See application file for complete search history.

(56) References Cited

U.S. PATENT DOCUMENTS

| 8,639,309 B2 * | 1/2014 | Shuler ................. A61B 5/1455 600/323 |
| 2004/0215072 A1 * | 10/2004 | Zhu ....................... G01S 15/899 600/407 |

(Continued)

FOREIGN PATENT DOCUMENTS

| FR | 2899889 A1 | 10/2007 |
| WO | 2013186780 A1 | 12/2013 |
| WO | 2020178522 A2 | 9/2020 |

OTHER PUBLICATIONS

Carovac et al.; "Application of Ultrasound in Medicine"; vol. 19 No. 3 Sep. 2011; pp. 168-171 (Year: 2011).*

(Continued)

*Primary Examiner* — Dixomara Vargas
(74) *Attorney, Agent, or Firm* — Barclay Damon LLP; Daniel McGrath

(57) ABSTRACT

Disclosed herein is a near-infrared imaging system for identifying a target feature in an object. The system comprises a near-infrared transmitter receiver array for transmitting near-infrared radiation into the object and receiving corresponding near-infrared radiation emitted from the object and a data processing system (215) configured to process near-infrared radiation received via the near-infrared transmitter receiver array in accordance with a near-infrared imaging model (216). The system further comprises signal transmitting means (205) arranged to transmit one or more further signals into the object; and signal receiving means (206) arranged to receive the one or more further signals from the object. The data processing system (215) is further configured to process one or more characteristics of the one or more further signals received by the signal receiving means (206) to generate one or more constraints (218) to apply to the near-infrared imaging model (216).

25 Claims, 8 Drawing Sheets

(56) References Cited

U.S. PATENT DOCUMENTS

| | | | |
|---|---|---|---|
| 2016/0022223 A1* | 1/2016 | Grundfest | A61B 5/02055 |
| | | | 600/407 |
| 2020/0367761 A1* | 11/2020 | Akbari | A61B 5/4875 |
| 2021/0338092 A1* | 11/2021 | Akbari | A61B 5/4866 |
| 2022/0031167 A1* | 2/2022 | Beldon | A61B 5/0075 |
| 2023/0181158 A1 | 6/2023 | Tisa et al. | |
| 2024/0115135 A1* | 4/2024 | Beldon | A61B 5/0042 |

OTHER PUBLICATIONS

Search Report in GB application No. 2101565.6 dated Oct. 26, 2021 (4 pages).

Zhu et al., "Near Infrared Diffusive Light Imaging with Ultrasound," Optics & Photonics, p. 31 (2001), 1 page.

* cited by examiner

NEAR-INFRARED IMAGING SYSTEM FOR IDENTIFYING A TARGET FEATURE IN AN OBJECT

CROSS REFERENCE TO RELATED APPLICATIONS

This is a national stage application filed under 37 U.S.C. 371 based on International Patent Application No. PCT/GB2022/050283, filed on Feb. 3, 2022 and entitled "NEAR-INFRARED IMAGING SYSTEM FOR IDENTIFYING A TARGET FEATURE IN AN OBJECT", which claims priority to United Kingdom Application No. 2101565.6, filed on Feb. 4, 2021, entitled "NEAR-INFRARED IMAGING SYSTEM FOR IDENTIFYING A TARGET FEATURE IN AN OBJECT", the contents of which are incorporated herein by reference in their entirety for all purposes.

TECHNICAL FIELD

The present invention relates to techniques for improving the accuracy of near-infrared (NIR) imaging systems.

BACKGROUND

Near-infrared imaging techniques such as near-infrared spectroscopy (NIRS) or tomography can be used to identify features within an object.

Near-infrared imaging techniques can be applied to neuroimaging to identify structural or functional features within a subject's head. In such applications, near-infrared radiation is transmitted into a subject's head and corresponding output radiation, which has propagated through the subject's head, is detected and analysed.

Information about the interior of the subject's head can be inferred from changes the NIR radiation undergoes as it propagates through the subject's head based, in particular, on the fact that NIR radiation is absorbed differently by oxygenated haemoglobin and deoxygenated haemoglobin.

Whilst the spatial resolution that can be achieved using certain NIRS based techniques is low compared to other imaging techniques such as computed tomography (CT), they are nevertheless considered a promising technique for rapidly identifying features indicative of pathologies such as intra-cranial hematomas.

In a typical example of NIRS, a headset comprising an array of optodes is placed on a subject's head. Each optode typically comprises a fibre optic element which is connected at one end in the headset to either a NIR transmitter or NIR receiver and is configured at the other end to contact the surface of the subject's head for either directing NIR radiation into the subject's head or for receiving NIR radiation that has propagated through the subject's head.

Output NIR radiation is detected and analysed to determine changes that the NIR radiation has undergone as it propagated through the subject's head. Corresponding parameters (for example signal attenuation and phase-shift) are input to a computing system running specially adapted data analysis software.

This data analysis software implements a mathematical, computational or machine learning model of the propagation path of the NIR radiation. By inputting the parameters from the detected output NIR radiation, characteristics of the region of the subject's head through which the radiation has propagated can be estimated. These characteristics can then be analysed to determine, for example, changes in blood oxygenation within the cortex indicative of activity levels within different regions of the brain, or whether the characteristics include features indicative of a target pathology such as an intra-cranial hematoma.

Such mathematical, computational or machine learning models are typically based on assumptions that the optodes have "ideal" contact with the surface of the subject's head. For example, it is assumed that optodes engage with the subject's head with consistent spacing and in a manner that ensures consistent coupling of the NIR radiation between the subject's head and the optodes. However, in practical implementations, variations in head shape and the fact that hair may get trapped between the optode and the surface of the subject's head means that ideal contact between the subject's head and the optodes may not be achieved. As a result, the accuracy with which characteristics of the region of the subject's head through which the radiation has propagated can be estimated, and the subsequent accuracy in determining whether or not features indicative of a target pathology are present, is reduced.

It is an object of certain embodiments of the invention to obviate or mitigate one or more of the above described disadvantages.

It is an object of certain embodiments to provide techniques that improve the accuracy with which near-infrared imaging models can be used to identify features indicative of target pathologies from data gathered using near-infrared imaging techniques.

SUMMARY OF THE INVENTION

In accordance with a first aspect of the invention there is provided a near-infrared imaging system for identifying a target feature in an object, said system comprising: a near-infrared transmitter receiver array for transmitting near-infrared radiation into the object and receiving corresponding near-infrared radiation emitted from the object, and a data processing system configured to process near-infrared radiation received via the near-infrared transmitter receiver array in accordance with a near-infrared imaging model to identify the presence or absence of the target feature within the object. The system further comprises: signal transmitting means arranged to transmit one or more further signals into the object; and signal receiving means arranged to receive the one or more further signals from the object. The data processing system is further configured to process one or more characteristics of the one or more further signals received by the signal receiving means to generate one or more constraints to apply to the near-infrared imaging model.

Optionally, the signal transmitting and signal receiving means comprise one or more ultrasound transducers and the one or more further signals comprise ultrasound signals.

Optionally, the near-infrared transmitter receiver array is an array of near-infrared signal generators and detectors each configured to make direct contact with a surface of the object.

Optionally, the near-infrared transmitter receiver array is an optode array comprising a plurality of optodes each having a distal end arranged to make contact with a surface of the object.

Optionally, the signal transmitting means is arranged to transmit the one or more further signals via one or more optodes of the optode array and the signal receiving means is arranged to receive the one or more further signals via one or more optodes of the optode array.

Optionally, the data processing system is configured to process one or more characteristics of the received one or more further signals to determine a level of contact between one or more optodes of the optode array and the surface of the object, and to generate one or more corresponding constraints to apply to the near-infrared imaging model.

Optionally, the data processing system is configured to process one or more characteristics of the received one or more further signals to determine a distance of a contact point of an optode via which the signal was transmitted from a contact point of an optode via which the signal was received, and to generate one or more corresponding constraints to apply to the near-infrared imaging model.

Optionally, the data processing system is configured to process one or more characteristics of the received one or more further signals to determine a distance of a contact point of an optode via which the signal was transmitted from a plurality of contact points of optodes via which the signal was received, and to generate one or more corresponding constraints to apply to the near-infrared imaging model.

Optionally, the data processing system is configured to process one or more characteristics of the received one or more further signals to determine a material composition of the object between a contact point of an optode via which the signal was transmitted and a contact point of an optode via which the signal was received, and to generate one or more corresponding constraints to apply to the near-infrared imaging model.

Optionally, the data processing system is configured to process one or more characteristics of the received one or more further signals to determine a thickness of an outermost layer or layers of the object, and to generate one or more corresponding constraints to apply to the near-infrared imaging model.

Optionally, the signal transmitting means is arranged to transmit one or more still further signals into the object, the still further signals comprising acoustic signals that cause periodic compression of a region of the object.

Optionally, the acoustic signals have a frequency of between 10 Hz and 100 kHz.

Optionally, the data processing system is configured to process near-infrared radiation received via the near-infrared transmitter receiver array to identify an amount of modulation present in the received near-infrared radiation caused by the periodic compression of the region of the object, and to generate one or more corresponding constraints to apply to the near-infrared imaging model.

Optionally, the signal transmitting and signal receiving means comprise one or more impedance measuring devices and the one or more signals comprise electrical signals.

Optionally, the electrical signals are transmitted and received via one or more electrodes associated with optodes of the array.

Optionally, the one or more electrodes are each coupled to the optode with which they are associated.

Optionally, each of the one or more electrodes is formed by an electrically conducting layer surrounding an optically transmissive core which forms the optode with which the electrode is associated.

Optionally, the system further comprises an insulating layer surrounding each electrically conducting layer.

Optionally, each electrode is formed by an electrically conducting core surrounded by an optically conducting outer layer that forms the optode with which the electrically conducting core is associated.

Optionally, the optically conducting outer layer substantially insulates the electrically conducting core.

Optionally, the optically conducting outer layer comprises a plurality of optode fibres.

Optionally, the data processing system is configured to perform a demodulation process on detected near-infrared radiation prior to processing the detected near-infrared radiation in accordance with the near-infrared imaging model.

Optionally, the target feature is a change in perfusion or liquid content of biological tissue.

Optionally, the target feature is indicative of a target pathology.

Optionally, the target pathology is an intracranial haematoma, intracranial haemorrhage, or change in blood flow, blood oxygenation or blood volume characteristic of cerebral ischaemia.

Optionally, the object is a subject's head.

Optionally, the object is a subject's foot or chest.

Optionally, the system is a near-infrared spectroscopy or near-infrared tomography system.

According to a second aspect of the invention there is provided a method of generating one or more constraints to apply to a near-infrared imaging model, the method comprising: transmitting, via a near-infrared transmitter receiver array, near-infrared radiation into an object; receiving, via the near-infrared transmitter receiver array, corresponding near-infrared radiation emitted from the object; transmitting one or more further signals into the object; receiving the one more further signals from the object; processing one or more characteristics of the received one or more further signals to generate one or more constraints to apply to the near-infrared imaging model; applying the one or more constraints to the near-infrared imaging model; and processing near-infrared radiation received via the near-infrared transmitter receiver array in accordance with the near-infrared imaging model to identify the presence or absence of a target feature within the object.

Optionally, the one or more further signals comprise electrical signals.

Optionally, the one or more further signals comprise ultrasound signals.

Optionally, the near-infrared transmitter receiver array is an optode array comprising a plurality of optodes each having a distal end arranged to make contact with a surface of the object.

Optionally, the one or more further signals are transmitted and received via one or more optodes of the optode array.

Optionally, the one or more further signals are transmitted and received via one or more electrodes associated with optodes of the array.

In accordance with certain embodiments of the invention, a near-infrared imaging system is provided comprising a near-infrared transmitter receiver array for positioning on an object such as a subject's head. In contrast with conventional systems, in addition to near-infrared radiation transmitting and receiving components, the system includes means to transmit and receive further signals via the array which, when received, can be analysed to generate one or more constraints which can be applied to modify the near-infrared imaging model used in the system to improve the accuracy of the output of the model. The further signals are typically non-optical signals such as ultrasound or electrical signals.

Advantageously, this enables the near-infrared imaging model to be adapted, based on the constraints, to take account of specific factors that can be determined using the detected further signals. These factors can include the positioning of the near-infrared transmitter receiver array on the object, whether or not (or the degree to which) individual components of the array are in contact with the object to enable NIR radiation to pass to and from the components of the array and the object, and the spacing between the components of the array, that depends on the unique shape of the object which the array is in contact with, amongst others.

In certain embodiments, the constraints are based on sensor measurements of material properties of the object. For example, in certain embodiments the constraints are based on sensor measurements of material properties associated with the propagation path through the object. In certain embodiments, the constraints are based on sensor measurements generated in response to non-near-infrared signals. In certain embodiments, the non-near-infrared signals are electrical or ultrasound signals.

The imaging model is generated from both the near-infrared signals and the non-near-infrared signals. That is, the constraints are used simultaneously with the near-infrared radiation received via the near-infrared transmitter receiver array to generate the near-infrared imaging model.

In certain embodiments, the near-infrared imaging model comprises a mathematical model of the propagation path of the near-infrared radiation and non-near-infrared signal (for example an ultrasound or electrical signal) passing through the object.

In certain embodiments, in the model the material properties at each node of a 3D mesh are modelled. Advantageously, constraining the model using simultaneous equations containing measurements of different types of material properties (optical absorption and scattering from the near-infrared signals, acoustic impedance from the ultrasound signals, electrical impedance from the electrical signals) allows higher fidelity models to be resolved. Leveraging the difference in material properties over different characteristics (optical, acoustic, electrical), and solving the model for both characteristics simultaneously, allows for imaging with greater resolution than a single domain or by solving two models one after the other.

In certain embodiments, the near-infrared imaging model comprises two components, a forwards model and an inverse model. The forwards model can simulate propagation of the near-infrared and non-near-infrared signals through the 3D mesh. The results of the forwards model can be compared to reality to generate an estimate of the error. The inverse model can update the 3D mesh to reduce the error in the forwards model. By iterating cycles of the forwards and inverse model, the 3D mesh can be made more accurate. Advantageously, by including the additional material properties (acoustic impedance; electrical impedance) in the 3D mesh, and solving forwards models for both properties, a single inverse model can be used to update the 3D mesh. In this way, the imaging model is generated based on both the near-infrared signals and the non-near-infrared signals.

Advantageously, in accordance with certain embodiments of the invention, the transmitted further signals can include acoustic signals that cause a periodic compression of the object. In such embodiments, different parts of the object experience a different degree of compression resulting from the transmitted further signals due to, for example, differences in material composition of parts of the object and/or the acoustic signals dissipating as the distance from the point where the acoustic signals were transmitted into the object increases. Such a periodic compression of the object modifies the NIR radiation transmitting properties of the object in a manner that results in a periodic change in amplitude of the detected NIR radiation that has passed through the region of the object that has been subject to the acoustic signals.

Advantageously, this can provide further data that can be used to generate constraints for the near-infrared imaging model to further improve the model accuracy, for example by enabling NIR radiation that has passed through shallower parts of the object to be distinguished from NIR radiation that has passed through deeper parts of the object.

Various further features and aspects of the invention are defined in the claims.

BRIEF DESCRIPTION OF THE DRAWINGS

Embodiments of the present invention will now be described by way of example only with reference to the accompanying drawings where like parts are provided with corresponding reference numerals and in which.

DETAILED DESCRIPTION

Figure 1:
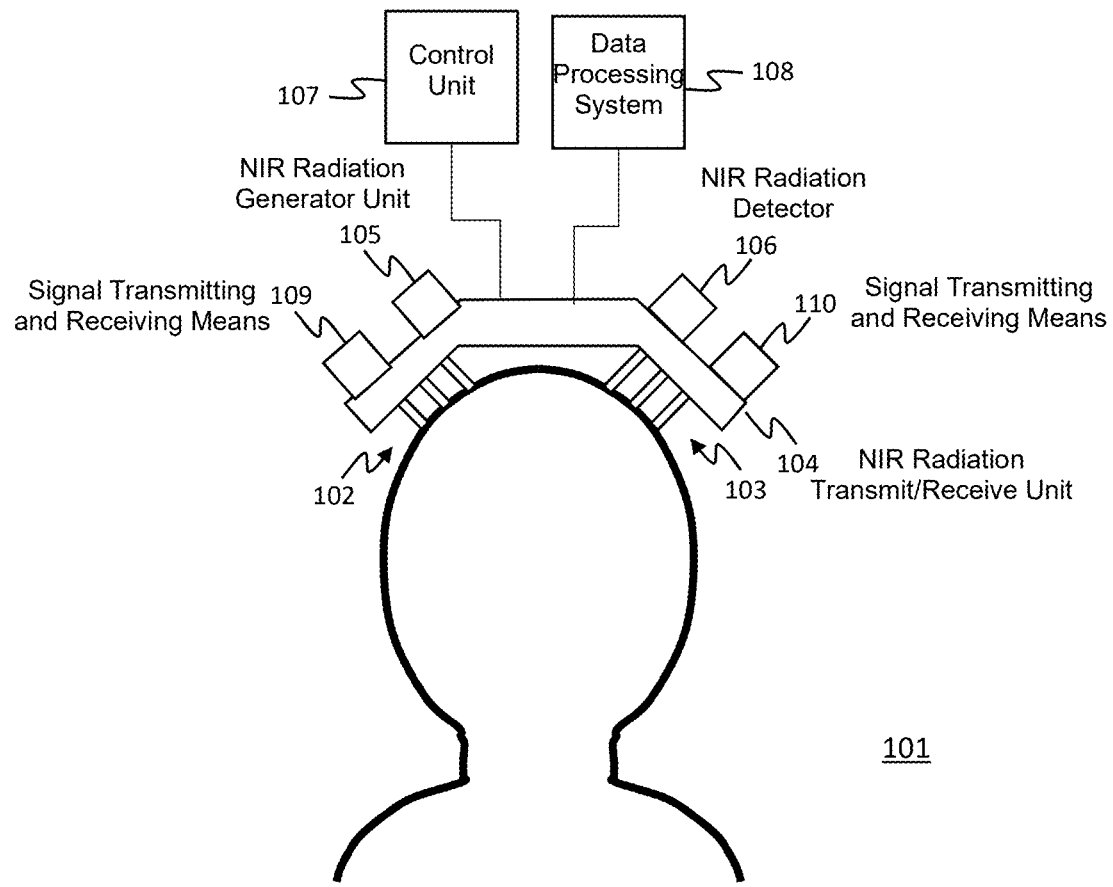
FIG. 1 provides a schematic diagram depicting a near-infrared spectroscopy system in accordance with certain embodiments of the invention for undertaking intra-cranial analysis of a subject.

FIG. 1 provides a schematic diagram depicting a near-infrared imaging system 101 for identifying a target feature in an object in accordance with certain embodiments of the invention. In this embodiment, the object is a subject's head, and the target feature is a feature indicative of the presence of a target pathology within the subject's head. Examples of target pathologies include an intracranial haematoma, intracranial haemorrhage, or change in blood flow, blood oxygenation or blood volume characteristic of intracranial ischaemia.

In this embodiment, the near-infrared imaging system 101 is a near-infrared spectroscopy (NIRS) system, such as a structural or functional NIRS (fNIRS) system.

In keeping with conventional systems, the system 101 comprises a near-infrared transmitter receiver array. The near-infrared transmitter receiver array is an optode array comprising a plurality of transmit optodes 102 and a plurality of receive optodes 103, which are coupled to NIR radiation transmit/receive unit 104 (provided, for example in a headset). The transmit/receive unit 104 comprises an NIR radiation generator unit 105 coupled to the transmit optodes 102 and an NIR radiation detector unit 106 coupled to the receive optodes 103. In use, the optode array is positioned on a subject's head.

NIR radiation is transmitted into the subject's head via the plurality of transmit optodes 102 and corresponding NIR radiation that has propagated through the subject's head is received by the plurality of receive optodes 103. Operation of the NIR radiation transmit/receive unit 104 and in particular the NIR radiation generator unit 105 and NIR radiation detector unit 106 is controlled by a control unit 107, typically provided by a suitably programmed computing device including a memory and processor.

It will be understood that near-infrared radiation that is transmitted and received is of a range of wavelengths suitable for imaging within an object, more particularly, in the context of imaging within a subject's head, for identifying the amounts of oxygenated and deoxygenated haemoglobin present in a region of the subject's head. In certain embodiments, the near-infrared radiation has a wavelength in the range of 600 nm-1100 nm, more preferably 650 nm-1050 nm, still more preferably 700 nm-900 nm. It will be understood that in certain embodiments, the near-infrared radiation can include radiation outside of these ranges, for example including shorter wavelength radiation overlapping with the visible light spectrum.

The transmit/receive unit 104 comprises componentry configured to generate output signals conveying data relating to the NIR radiation received by the receive optodes 103 and detected by the NIR radiation detector unit 106. These output signals are communicated via a suitable signal line to a data processing system 108, typically provided by a suitable programmed computer.

In certain embodiments, the system can be used to identify a target feature within an object such as a change in perfusion or liquid content of biological tissue.

Figure 7:
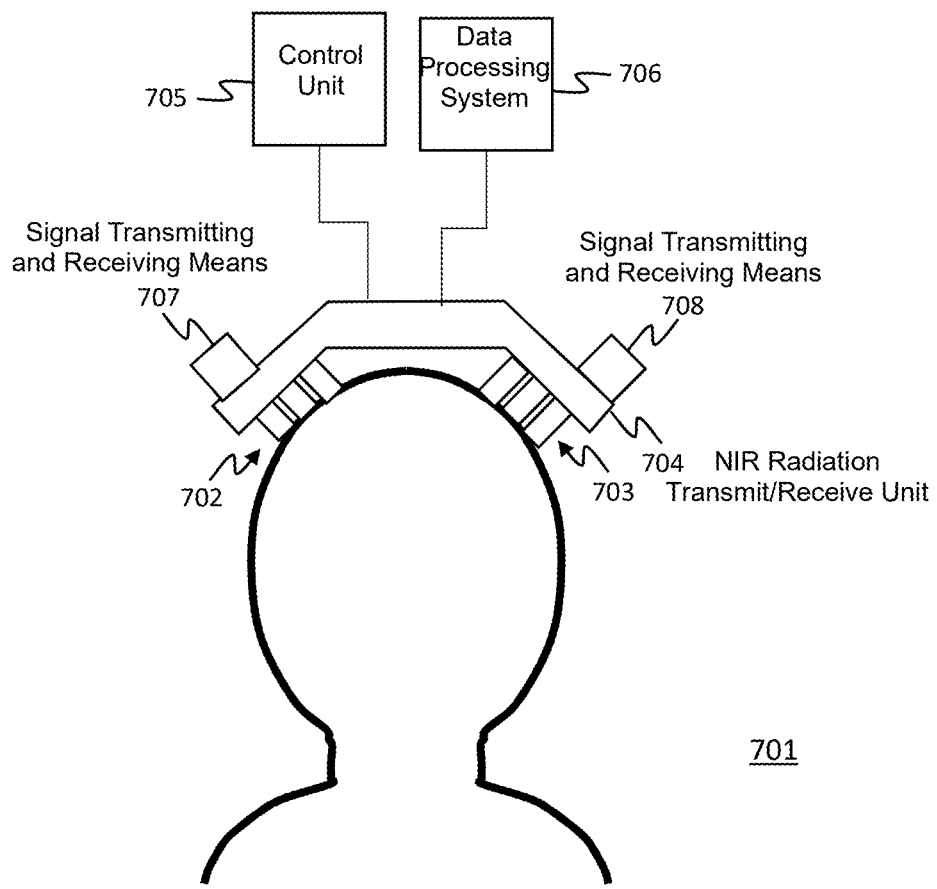
FIG. 7 provides a schematic diagram depicting a near-infrared imaging system for identifying a target feature in an object in accordance with certain embodiments of the invention.

In certain embodiments, rather than including an optode array, the system 101 can be arranged so that NIR signal generating and detecting components make direct contact with the subject's head. Such an arrangement is shown in FIG. 7.

It will be understood that with suitable modification, the system can be used to image other objects such as a subject's feet or chest.

The data processing system 108 is configured to analyse the data detected by the NIR radiation detector unit 106 using a near-infrared spectroscopy imaging model to generate output data relating to the region of the subject's head through which the NIR radiation has propagated, for example, output data indicating whether or not features indicative of a target pathology are present.

In certain embodiments, the data processing system 108 is configured to perform a demodulation process on the data generated by the NIR radiation detector unit before the data is analysed by the near-infrared spectroscopy imaging model. The demodulation process can be used to reduce noise present in the data and thereby improve the imaging model accuracy.

In such embodiments, the near-infrared radiation signals generated by the NIR radiation generator unit are modulated in amplitude. Typically, such modulation follows a continuous frequency sine wave profile.

The data processing system is configured to perform a demodulation process on data from the NIR radiation detector unit corresponding to the received signal. The demodulation process involves multiplying the received signal by a carrier signal having the same frequency as the modulation signal. The resulting signal is then filtered to obtain the demodulated signal.

However, in contrast with conventional systems, the system shown in FIG. 1 is provided with further signal transmitting and signal receiving means 109, 110. The further signal transmitting and receiving means 109, 110 are configured to respectively transmit and receive further signals via the optode array. The further signals are typically non-optical signals. Data relating to the received further signals is then communicated to the data processing system 108 and used to generate model constraints to modify the near-infrared spectroscopy imaging model to take account of variations in the way that the optode array is engaged with the subject's head.

Further specific embodiments are described in more detail with reference to FIG. 2 and FIG. 3.

Ultrasound Example Embodiment

Figure 2:
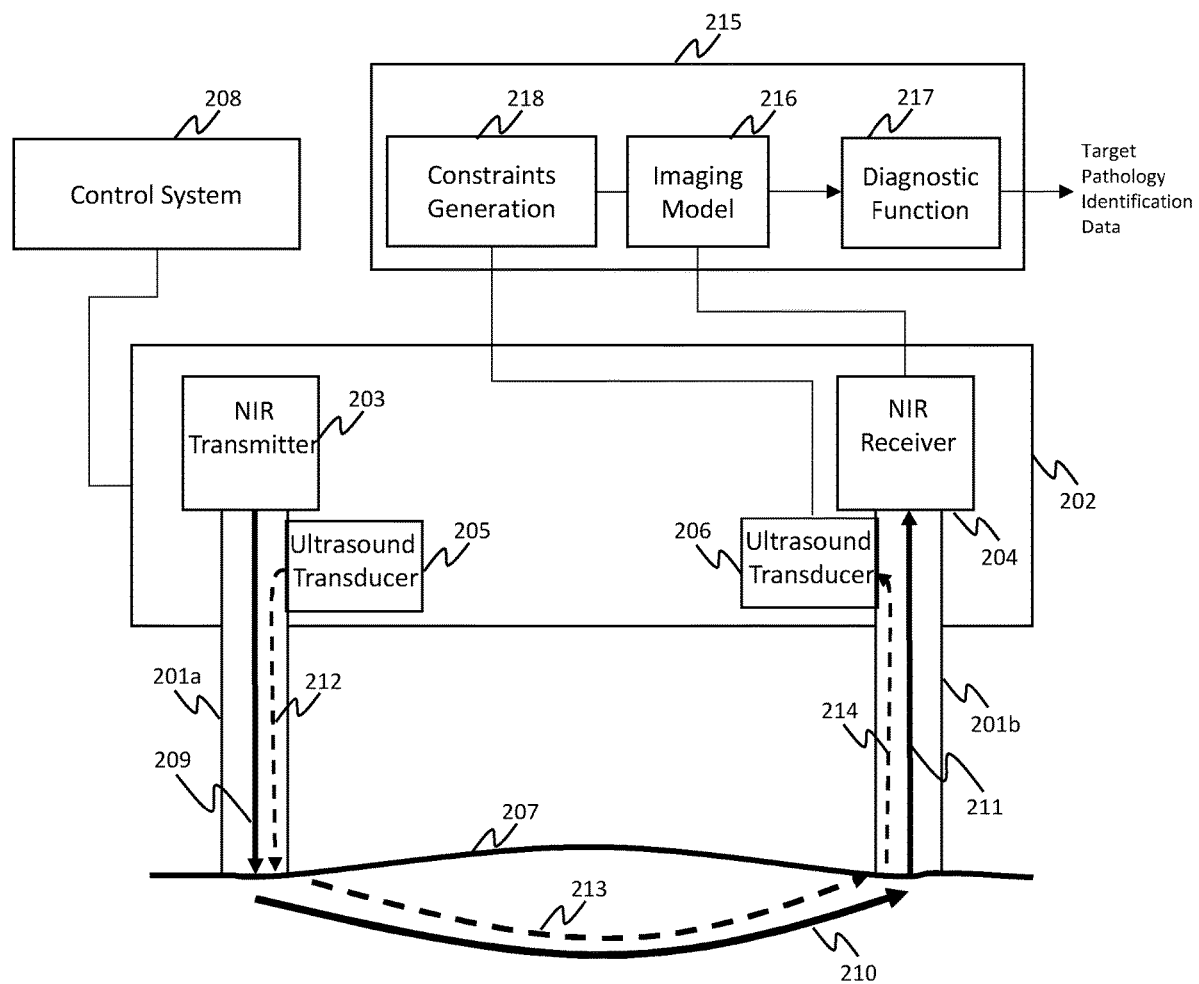
FIG. 2 provides a schematic diagram depicting a near-infrared spectroscopy system in accordance with certain embodiments of the invention for undertaking intra-cranial analysis of a subject using ultrasound signals to generate constraints for a NIR model.

FIG. 2 provides a schematic diagram depicting an example of a near-infrared spectroscopy system for imaging a subject's head in accordance with certain embodiments of the invention.

The system includes a transmitter receiver array provided by an array of optodes, which are coupled to a signal transmit/receive unit 202. The array of optodes comprises a transmit optode 201*a* and a receive optode 201*b*. Typical implementations will comprise a plurality of transmit optodes and a corresponding plurality of receive optodes. However, for simplicity only a single transmit and receive optode are shown in FIG. 2.

Coupled to one end of the transmit optode 201*a* (a proximal end of the optode 201*a*) in the transmit/receive unit 202 is a NIR transmitter unit 203 configured to generate NIR radiation and direct this into the transmit optode 201*a*. Coupled to one end of the receive optode 201*b* (a proximal end of the optode 201*b*) in the transmit/receive unit 202 is a NIR receiver unit 204 configured to detect NIR radiation received at the receive optode 201*b*.

Coupled to the transmit optode 201*a* in the transmit/receive unit 202 is signal transmitting means in the form of a first ultrasound transducer 205 configured to transmit ultrasound energy into the transmit optode 201*a*. Correspondingly, coupled to the receive optode 201*b* in the transmit/receive unit 202 is signal receiving means in the form of a second ultrasound transducer 206 configured to detect ultrasound energy transmitted through the receive optode 201*b*.

In use, the optode array is brought into contact with the surface 207 of a subject's head. The distal ends of the optodes of the optode array make contact with the surface 207 of the subject's head. Under the control of a control system 208, the NIR transmitter 203 is configured to transmit a predetermined pattern of NIR radiation into the transmit optode 201*a*, which guides the NIR radiation through the transmit optode 201*a* (shown as a first solid line 209) to the surface 207 of a subject's head. The NIR radiation is then absorbed through the surface 207 of the subject's head and propagates through a region of the subject's head (shown as a second solid line 210). NIR radiation that has propagated through the region of the subject's head reaches a point of the subject's head where the receive optode 201b contacts the surface 207 and is guided through the receive optode 201b (shown as a third solid line 211) to the NIR receiver unit 204. The NIR receiver unit 204 is configured to generate an output signal corresponding to the received NIR radiation and communicate this to a data processing unit 215.

Further, under the control of the control system 208, the first ultrasound transducer 205 is configured to generate further signals in the form of ultrasound energy and transfer this into the transmit optode 201a. The ultrasound energy propagates through the transmit optode 201a (shown as a first broken line 212) and is transferred into the subject's head at the point on the surface 207 where the transmit optode 201a contacts the surface 207. The ultrasound energy propagates through the region of the subject's head (shown as a second broken line 213) and is transferred into the receive optode 201b at the point where the receive optode 201b contacts the surface 207. The ultrasound energy is then transferred through the receive optode 201b (shown as a third broken line 214) and is received at the second ultrasound transducer 206. The second ultrasound transducer 206 is configured to generate an output signal corresponding to the received ultrasound energy and communicate this signal to the data processing unit 215.

Typically, the frequency of the ultrasound signals generated by the first ultrasound transducer 205 is in the region of approximately 1 MHz to 100 MHz.

The region of the subject's head that the signals pass through typically includes one or more of the subject's scalp, skull, blood, cerebrospinal fluid, and white and grey brain matter.

NIR radiation is also referred to herein as "NIR light".

The data processing unit 215 has running thereon software implementing an imaging model function 216.

The imaging model function 216 implements a mathematical model of the propagation path through the region of the subject's head. The mathematical model is configured to generate estimates of characteristics of the propagation path based on changes that a known signal has undergone as it has propagated through the region of the subject's head. In certain embodiments, the imaging model function 216 implements a computational or machine learning model of the propagation path through the region of the subject's head.

These characteristics can then be used to determine whether or not features indicative of a target pathology are present in the propagation path.

More specifically, the imaging model function is configured to compare differences between the NIR radiation generated by the NIR transmitter unit 203 and the NIR radiation detected by the NIR receiver unit 204 to determine changes that the NIR radiation has undergone as it propagates through the region of the subject's head.

These changes (typically signal attenuation, phase shifts and frequency shifts) are then quantized and input to the mathematical model to generate output characteristics corresponding to estimates of the characteristics of the propagation path—i.e. characteristics of the region of the subject's head through which the NIR radiation has propagated.

In certain embodiments, the mathematical model includes a 3D wireframe model of a subject's head. A finite element method (FEM) technique can be applied to the 3D model to determine the intensity and scattering of NIR radiation as it passes through the region of the subject's head.

The output characteristics are input to a diagnostic function 217 (also provided by software running on the data processing unit 215) which is configured to determine if they are indicative of the presence of a target pathology.

The accuracy of the mathematical model of the propagation path can be improved if further information is provided that can add further "constraints" to the model (for example modifying variables of differential equations which form part of the model). Examples of such constraints includes information about the spacing between the point where the transmit optode 201a contacts the surface 207 and the point where the receive optode 201b contacts the surface 207; the material of which the propagation path comprises (for example, mainly bone tissue) and the degree to which the transmit optode 201a and/or the receive optode 201b are in contact (and therefore coupled for transferring NIR radiation) with the surface 207 (for example, if one or both optodes 201a, 201b are only loosely in contact with the surface 207 due to hair fibres present between where the optodes 201a, 201b and the surface 207).

In order to generate data which can be used to provide such constraints, the data processing unit 215 has running thereon software providing a constraints generating function 218.

The constraints generating function 218 is configured to receive data from the output signal of the second transducer 206 and use this to infer characteristics associated with the propagation path from which constraints data can be generated.

For example, the constraints generating function 218 is configured to analyse the ultrasound energy received by the second ultrasound transducer 206 to determine a propagation time (e.g. the period of time taken for an ultrasound pulse to propagate through the propagation path) and thereby generate constraint data indicative of a distance between the transmit optode 201a and the receive optode 201b.

The constraints generating function 218 may be further configured to analyse the ultrasound energy received by the second ultrasound transducer 206 to determine signal attenuation data which is indicative of material present in the propagation path (for example, bone tissue and brain tissue attenuate ultrasound differently) and generate constraint data indicative of an estimated material composition of the propagation path.

The constraints generating function 218 may be further configured to analyse the ultrasound energy received by the second ultrasound transducer 206 to identify substantial amounts of signal attenuation (for example, total or almost total attenuation) indicative of the transmit optode 201a and/or the receive optode 201b not optimally in contact with the surface 207 and generate constraint data indicative of whether or not the transmit optode 201a and the receive optode 201b are estimated to be in optimal or sub-optimal contact with the surface 207.

The constraints generating function 218 may be further configured to analyse the ultrasound energy received by the second ultrasound transducer 206 to estimate the thickness of the outermost layer or layers of a subject's head (for example the scalp thickness) and to generate corresponding constraint data.

When the constraints generating function 218 has generated the constraint data, it is configured to communicate the constraint data to the imaging model function 216 which is configured to adapt the mathematical model accordingly.

For example, if the constraint data indicates that the transmit optode 201a and the receive optode 201b are separated by a particular distance, components of the mathematical model relating to the length of the propagation path are modified accordingly. Further, for example, if the constraint data indicates that the material of which the region of the subject's head comprises is principally, for example, bone tissue, components of the mathematical model relating to the material of which the propagation path is composed is modified accordingly. Further, for example if the constraint data indicates that the transmit optode 201a and/or the receive optode 201b are not in optimal contact with the surface 207, the diagnostic function 217 may enter a null result mode in which the signal from the NIR receiver 204 is disregarded for analysis.

In certain embodiments, the constraints are based on sensor measurements of material properties of the object. For example, in certain embodiments the constraints are based on sensor measurements of material properties associated with the propagation path through the object.

As described, the constraints are based on sensor measurements generated in response to non-NIR signals. In certain embodiments, the non-NIR signals are electrical or ultrasound signals. The constraints are used simultaneously with the near-infrared radiation received via the near-infrared transmitter receiver array to generate the near-infrared imaging model.

The near-infrared imaging model comprises a mathematical model of the propagation path of the near-infrared radiation and non-NIR signal (for example an ultrasound or electrical signal) passing through the object.

In certain embodiments, in the model the material properties at each node of a 3D mesh are modelled. Advantageously, constraining the model using simultaneous equations containing measurements of different types of material properties (optical absorption and scattering from the NIR signals, acoustic impedance from the ultrasound signals, electrical impedance from the electrical signals) allows higher fidelity models to be resolved. Leveraging the difference in material properties over different characteristics (optical, acoustic, electrical), and solving the model for both characteristics simultaneously, allows for imaging with greater resolution than a single domain or by solving two models one after the other.

In certain embodiments, the near-infrared imaging model comprises two components, a forwards model and an inverse model. The forwards model can simulate propagation of the near-infrared and non-NIR signals through the 3D mesh. The results of the forwards model can be compared to reality to generate an estimate of the error. The inverse model seeks to update the 3D mesh to reduce the error in the forwards model. By iterating cycles of the forwards and inverse model, the 3D mesh can be made more accurate. Advantageously, by including the additional material properties (acoustic impedance; electrical impedance) in the 3D mesh, and solving forwards models for both properties, a single inverse model can be used to update the 3D mesh. In this way, the imaging model is generated based on both the near-infrared signals and the non-NIR signals.

For simplicity, the embodiment shown in FIG. 2 has been described with reference to a single transmit optode 201a and receive optode 201b and their associated ultrasound transducers 205, 206. However, as noted above, in typical implementations, the system is provided with an array comprising a plurality of optodes.

In such implementations, ultrasound energy can be transmitted via a first optode of the array and detected at a plurality of other optodes of the array. The ultrasound transducers associated with each optode can generate respective output signals corresponding to received ultrasound energy and communicate these signals to the constraints generating function 218.

In such embodiments, the constraints generating function 218 may be further configured to analyse the ultrasound energy received by the plurality of ultrasound transducers to determine a propagation time from a transmit optode to a plurality of receive optodes and thereby generate corresponding constraint data defining the relative positions of the plurality of optodes.

In the technique described with reference to FIG. 2, the first ultrasound transducer 205 is used to transmit ultrasound energy and the second ultrasound transducer 206 is used to detect ultrasound energy. It will be understood that the ultrasound transducers 205 206 can operate as both ultrasound transmitters and receivers by transmitting ultrasound energy into a region of a subject's head and subsequently detecting corresponding ultrasound energy received from the region of the subject's head.

Figure 6:
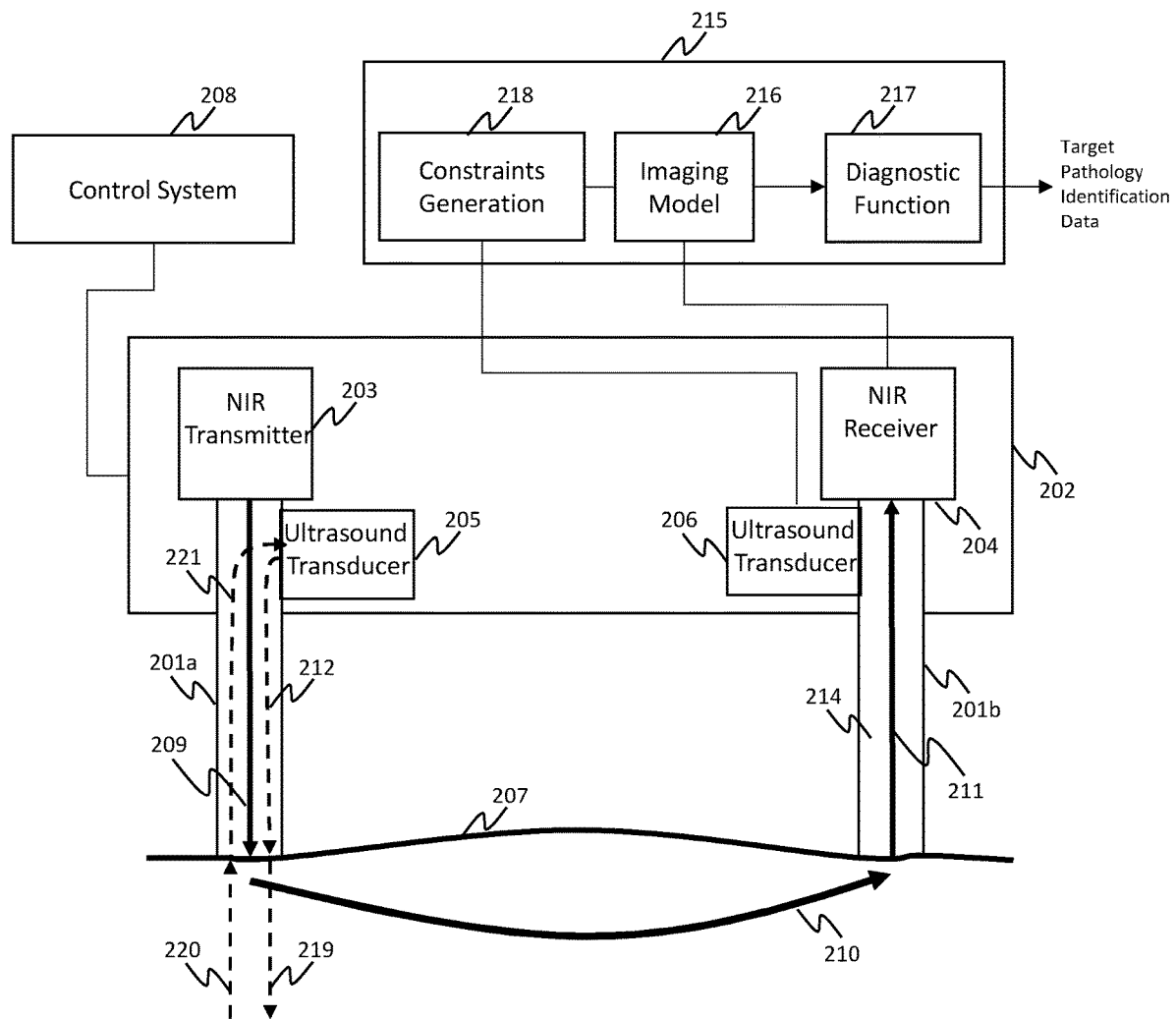
FIG. 6 depicts the near-infrared spectroscopy system of FIG. 2 operating in a manner where the first ultrasound transducer operates to both transmit and receive ultrasound signals.

FIG. 6 depicts the NIRS system of FIG. 2 operating in a manner where the first ultrasound transducer 205 operates to both transmit and receive ultrasound signals.

Under the control of the control system 208, the first ultrasound transducer 205 is configured to generate ultrasound energy and transfer this into the transmit optode 201a. The ultrasound energy propagates through the transmit optode 201a (shown as a first broken line 212) and is transferred into the subject's head at the point on the surface 207 where the transmit optode 201a contacts the surface 207. The ultrasound energy propagates through the region of the subject's head (shown as second and third broken lines 219 220) and returns to the transmit optode 201a. The ultrasound energy is then transferred through the transmit optode 201a (shown as a fourth broken line 221) and is received at the first ultrasound transducer 205. The first ultrasound transducer 205 is configured to generate an output signal corresponding to the received ultrasound energy and communicate this signal to the data processing unit 215.

Transmitting and receiving ultrasound energy via the same optode in this way can be particularly advantageous for estimating the thickness of the outermost layer or layers of a subject's head (for example the scalp thickness) via the constraints generating function 215 and generating corresponding constraint data.

Returning to FIG. 2, it will be understood that suitable signal processing steps can be performed on ultrasound signals received by the ultrasound transducers. Typically, such signal processing techniques are performed by the data processing unit 215.

For example, an averaging technique can be applied to signals received by the ultrasound transducers. This can help reduce noise from real world effects in the detected data.

Alternatively or additionally, a Gaussian fitting technique can be applied to signals received by the ultrasound transducers. This can help remove outliers in the ultrasound signals. Such outliers can be caused by errors as a reading is taken such as the subject's head moving as a reading is taken.

Figure 3:
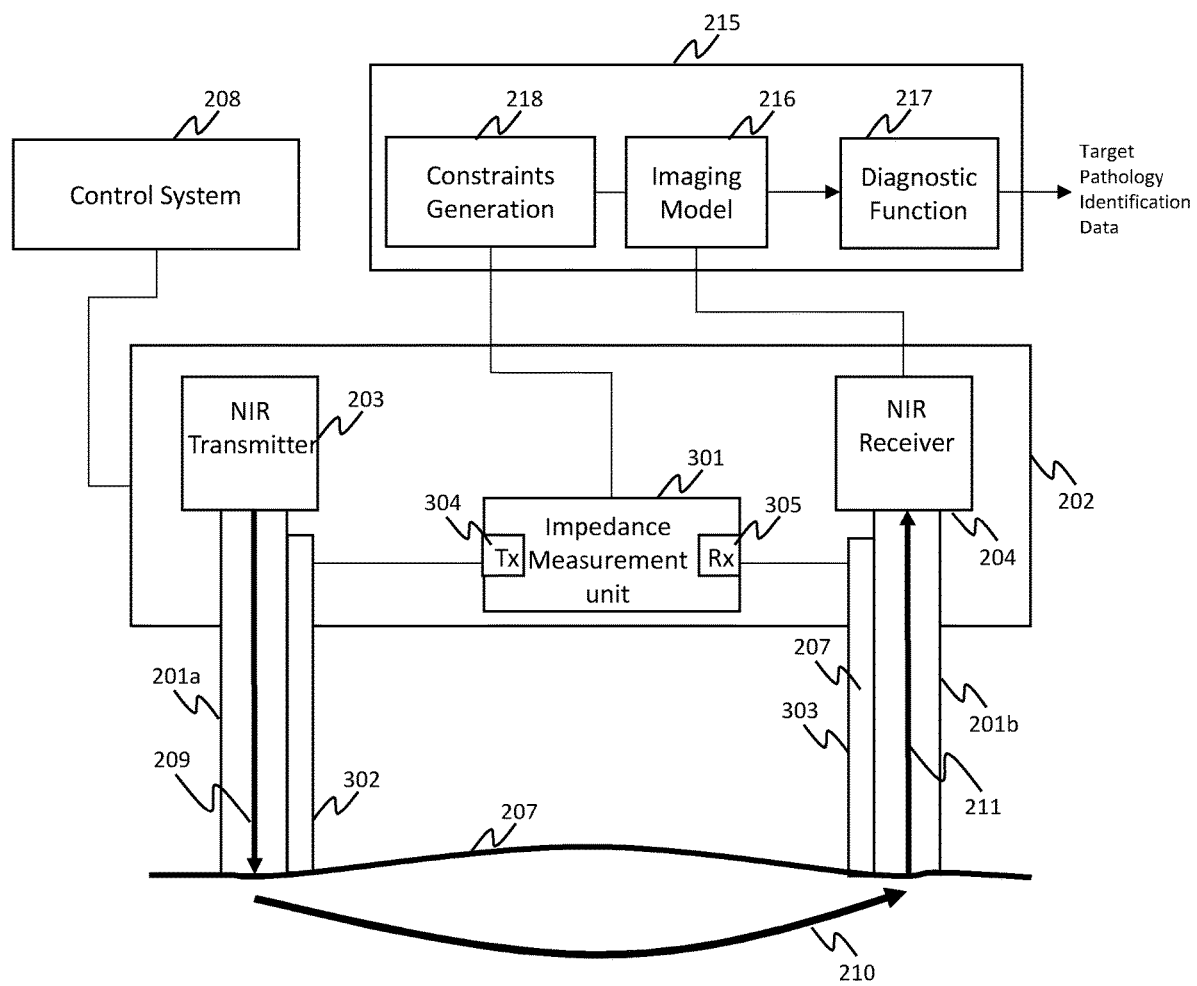
FIG. 3 provides a schematic diagram depicting a near-infrared spectroscopy system in accordance with certain embodiments of the invention for undertaking intra-cranial analysis of a subject using impedance to generate constraints for a NIR model.

FIG. 3 provides a schematic diagram depicting an example of a near-infrared spectroscopy system for imaging a subject's head in accordance with further embodiments of the invention.

The system depicted in FIG. 3 corresponds with the system described with reference to FIG. 2, except that rather than using further signals in the form of ultrasound energy to generate the constraint data, instead the further signals are electrical signals and the impedance is measured between the transmit and receive optodes 201a, 201b.

In use, the components of the system common with the embodiment described in FIG. 2 operate in a corresponding manner. That is, NIR radiation is transmitted by the NIR transmitter 203 to the NIR receiver 204 via the transmit and receive optodes 201a, 201b and the propagation path. The signal generated by the NIR receiver 204 is used by the imaging model to generate characteristics of the propagation path enabling the diagnostic function 217 to determine whether or not a target pathology is present in the region of the subject's head through which the propagation path passes.

However, rather than first and second ultrasound transducers, instead the system is provided with signal transmitting and receiving means in the form of an impedance measurement unit 301 coupled to a transmit electrode 302 which in turn is connected to the transmit optode 201a, and a receive electrode 303 which in turn is connected to the receive optode 201b.

In use, under the control of the control system 208, the impedance measurement unit 301 is configured to measure the impedance between the transmit electrode 302 and the receive electrode 303 and output a signal corresponding to the measured impedance to the data processing unit 215. This is typically achieved by inputting an electrical signal into the transmit electrode 302 from an electrical signal generator 304 in the impedance measurement unit 301, and measuring a corresponding electrical signal received by the receive electrode 303 using an electrical signal receiver 305 in the impedance measurement unit 301.

The constraints generating function 218 is configured to receive impedance measurement data from the impedance measurement unit 301 and use this to infer characteristics associated with the propagation path from which constraints data can be generated.

For example, the constraints generating function 218 is configured to analyse the impedance data to determine a distance between the transmit optode 201a and the receive optode 201b because the greater the distance, the higher the impedance. In such a case, the constraints generating function 218 may be configured to generate constraint data indicative of a distance between the transmit optode 201a and the receive optode 201b.

The constraints generating function 218 may be further configured to analyse the impedance data to identify very high or effectively infinite impedance between the transmitter electrode 302 and the receiver electrode 303 indicating that the transmit optode 201a and/or the receive optode 201b are not optimally in contact with the surface 207. In such a case, the constraints generating function 218 may be configured to generate constraint data indicative of whether or not the transmit optode 201a and the receive optode 201b are estimated to be in optimal or sub-optimal contact with the surface 207.

As described above, when the constraints generating function 218 has generated the constraints data, it is configured to communicate the constraints data to the imaging model function 216 which is configured to adapt the mathematical model accordingly.

Figure 5:
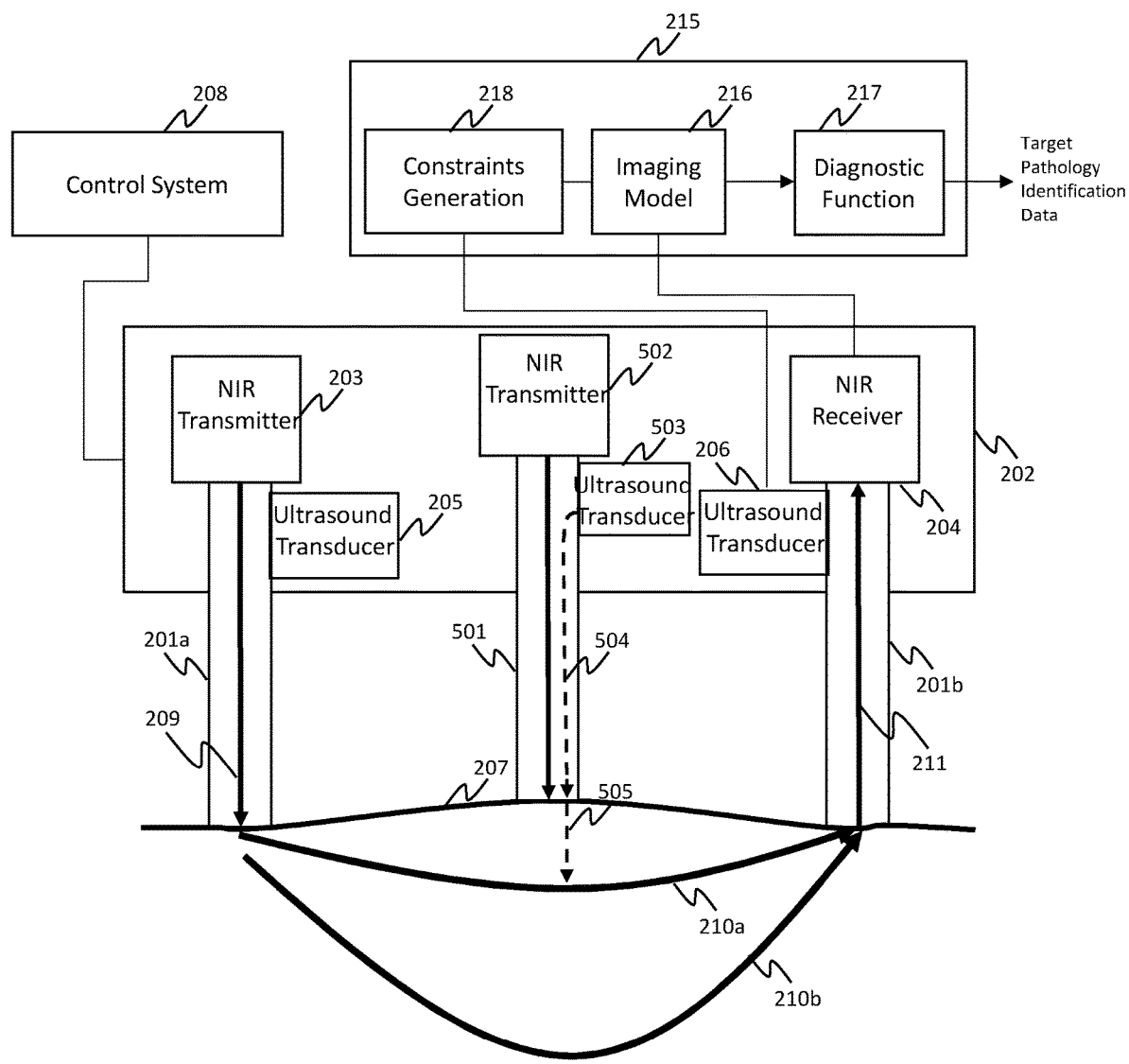
FIG. 5 provides a schematic diagram depicting a near-infrared spectroscopy system in accordance with certain embodiments of the invention for undertaking intra-cranial analysis of a subject using acoustic signals to cause periodic compression to generate corresponding NIR signals to generate constraints for a NIR model.

FIG. 5 provides a schematic diagram depicting an example of a near-infrared spectroscopy system for imaging a subject's head in accordance with further embodiments of the invention.

The system depicted in FIG. 5 corresponds with the system described with reference to FIG. 2 except that a further optode 501 of the optode array is shown. Similar to the transmit optode 201a, the further optode 501 has an associated NIR transmitter 502 and ultrasound transducer 503. The further optode 501 operates in a corresponding manner as the transmit optode 201a.

In use, the components of the system common with the embodiment described in FIG. 2 operate in a corresponding manner. That is, NIR radiation is transmitted by the NIR transmitter 203 to the NIR receiver 204 via the transmit and receive optodes 201a, 201b and the propagation path. The signal generated by the NIR receiver 204 is used by the imaging model to generate characteristics of the propagation path enabling the diagnostic function to determine whether or not a target pathology is present in the region of the subject's head through which the propagation path passes.

The propagation path between the transmit optode 201a and receive optode 201b is shown in more detail in FIG. 5 (compared with FIG. 2). As can be seen, the propagation path includes a shallower portion 210a and a deeper portion 210b. NIR light propagating through the shallower portion 210a passes closer to the surface of the subject's head (typically through the subject's scalp region) and NIR light propagating through the deeper portion 210b passes deeper within the subject's head (typically through the subject's skull and brain).

Under the control of the control system 208, the ultrasound transducer 503 is configured to generate further acoustic signals and transfer these signals into the further optode 501. The acoustic signals are arranged to cause a periodic compression of tissue that they pass through.

The acoustic signals propagate through the further optode 501, as shown by the first vertical broken line 504, and are transferred into the subject's head as acoustic energy at the point where the further optode 501 contacts the surface 207.

The acoustic energy propagates into the subject's head, as shown by the second vertical broken line 505.

Due to differences in the physical properties of layers of tissue of the subject's head, the region of the subject's head closest to the surface (the shallower portion), which is typically scalp tissue, experiences a significantly greater degree of physical excitation from the acoustic energy compared with the deeper portion of the subject's head (typically skull and brain tissue).

The physical excitation from the acoustic energy in the shallower portion of the subject's head causes localised changes in the density of the tissue in the form of periodic compression of the tissue at a frequency corresponding to the modulation frequency of the acoustic signals. These changes in tissue density cause corresponding changes in the NIR light transmission properties of the tissue when NIR light passes through the tissue.

The physical process whereby acoustic energy causes changes in the light transmission properties of a material is known as the acousto-optic effect.

NIR light propagating through the shallower portion 210a of the propagation path passes through a region of the scalp where more acoustic energy is present. The localised changes in tissue density caused by the acoustic energy causes a greater amount of modulation (i.e. varying of one or more properties of the waveform) of NIR light propagating through the shallower portion 210a.

In contrast, NIR light propagating through the deeper portion 210b of the propagation path passes through a region of the subject's head (typically the skull and brain) where less or no modulation of the NIR light occurs.

In this way, NIR light passing through shallower regions of the subject's head is "tagged" in a manner that allows further information to be generated for inputting into the imaging model, for example by allowing such "shallower" NIR light to be separated from NIR light passing through deeper regions of the subject's head.

In such embodiments, the control system 208 is configured to control the ultrasound transducer 503 to generate suitable acoustic energy signals that cause modulation of NIR light as it passes through the shallower portion of the subject's head. In such embodiments, the ultrasound transducer 503 is capable of generating lower frequency acoustic signals. For example, the acoustic signals can be sine wave signals in the range of approximately 10 Hz-100 KHz.

In such embodiments, the data processing unit 215 can be further configured to perform a demodulation process on NIR light detected via the receive optode 201*b* whereby an amount of modulation resulting from the effect of the acoustic energy on the NIR light is identified. Such a demodulation process is typically performed based on the modulation characteristics expected to result from the acoustic signals transmitted by the ultrasound transducer 503.

For example, if the acoustic signals generated by the ultrasound transducer are sine wave signals in the range of approximately 10 Hz-100 KHz, this causes a corresponding sine wave modulation to the NIR light at the same frequency as the applied signal, which can be identified during the demodulation process.

The amount of modulation of the NIR light is indicative of the portion of the subject's head that the NIR light has passed through. As described above, NIR light passing through the subject's scalp will typically have a higher amplitude of modulation whereas NIR light passing through deeper regions of the subject's head will typically have a lower or no amplitude of modulation.

The amplitude of modulation of the NIR light can also be indicative of other characteristics such as the properties of the material the NIR light has passed though and/or the degree of physical contact between one or more optodes and the surface of the subject's head.

It will be understood that suitable techniques can be used to demodulate the NIR light detected via the receive optode 201*b*. For example, a sine wave multiplication technique can be used. Alternatively, the detected signals can undergo a fast Fourier transform (FFT) step, followed by a filter step, followed by an inverse fast Fourier transform (IFFT) step.

Data obtained by the process of demodulating the NIR light can then be supplied to the constraints generating function 218 and/or into the imaging model function 216. The constraints generating function 218 can be further configured to analyse the data to generate corresponding constraint data for communicating to the imaging model function 216. For example, such constraint data may comprise information labelling certain inputs to the model as relating to NIR light that has passed through a subject's scalp and other inputs to the model as relating to NIR light that has passed through other parts of a subject's head, properties of the material the NIR light has passed though and/or the degree of physical contact between one or more optodes and the surface of the subject's head.

Advantageously, this can further improve the accuracy of the imaging model.

Embodiments of Optodes with Conductors

As described above, in certain embodiments, the transmit and receive optodes are each connected to corresponding electrodes. Such optode/electrode arrangements can be configured in a number of ways.

Typically, such arrangements are configured such that when the optode is in contact with the surface of a subject's head in such a manner that there is sufficient coupling to allow NIR radiation to be transferred from the optode into the subject's head, then the electrode is also in electrical contact with the subject's head. This is typically achieved by the electrode running the length of the optode and terminating at the same point the optode terminates at a distal end of the optode.

Figure 4A:
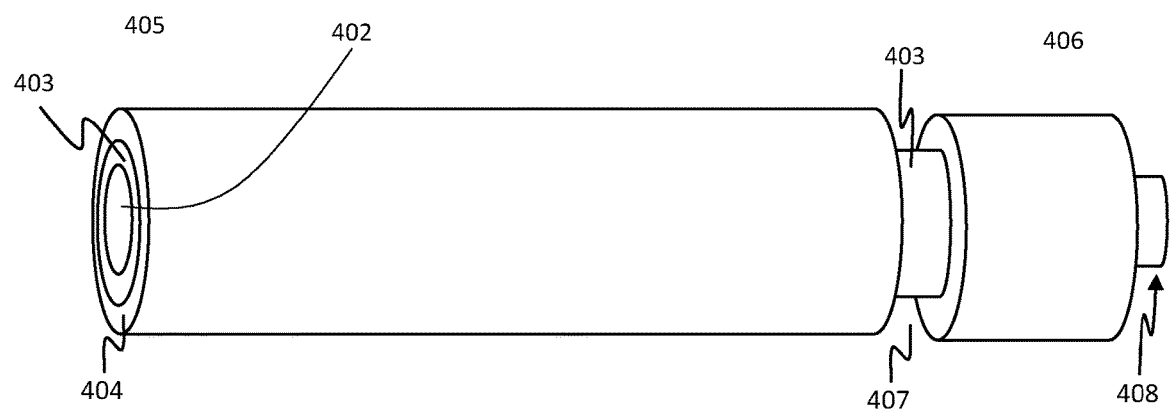
FIGS. 4a and 4b provide schematic diagrams depicting example optode arrangements in accordance with certain embodiments of the invention.

FIG. 4*a* provides a schematic diagram depicting the structure of an optode/electrode arrangement 401 in accordance with certain embodiments of the invention.

The arrangement comprises an optically transmissive core 402, typically comprising glass (silica) fibre which forms the optode. The optically transmissive core 402 is coated with a conductor layer 403, provided, for example by copper or similar conductive material and which forms the electrode. The conductor layer 403 is coated in an insulating outer layer 404, made from a suitable insulating material such as polyethylene.

The distal end 405 of the optode arrangement 401 is configured to contact the surface of a subject's head. As can be seen, the optically transmissive core 402 and the conductor layer 403 terminate at substantially the same point along the axis of the optode arrangement 401 thus ensuring that the optically transmissive core 402 and the conductor layer 403 will be brought into contact with the surface of the subject's head at same time, and to the same degree, when the optode arrangement 401 is positioned on the subject's head.

The proximal end 406 of the optode arrangement can be configured in any suitable way enabling the conductor layer 403 to be connected to the impedance measuring unit and the optically transmissive core 402 to be connected to the NIR transmitter or receiver unit. In the example depicted in FIG. 4*a*, the proximal end 406 of the optode arrangement 401 is configured so that the conductor layer 403 can be connected to the impedance measuring unit via an opening 407 and the optically transmissive core 402 extends onwards 408 for engagement with an optical element for directing the NIR radiation from a NIR transmitter unit (if the optode arrangement 401 is used as a transmit optode) or to a NIR receiver unit (if the optode arrangement 401 is used as a receive optode).

Figure 4B:
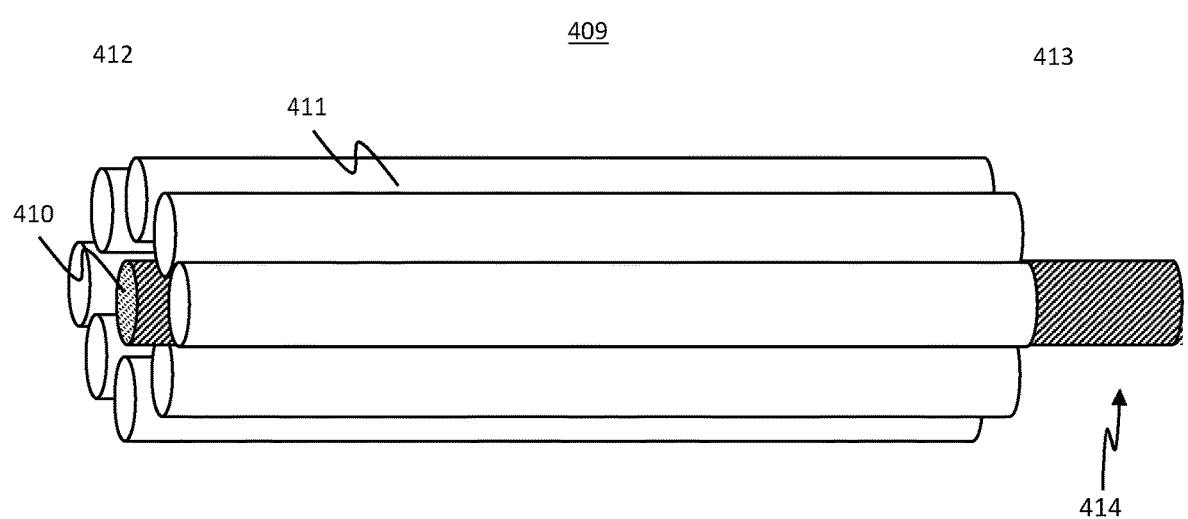

FIG. 4*b* provides a schematic diagram depicting the structure of an optode/electrode arrangement 409 in accordance with further embodiments of the invention. The arrangement 409 comprises an electrically conducting core 410, typically comprising copper or similar conducting metal which forms the electrode. Surrounding the electrically conducting core 410 are a plurality of optically conducting fibres 411 which together form the optode. Because the plurality of optically conducting fibres 411 surround the electrically conducting core 408 they act to insulate the electrode formed by the electrically conducting core 408. The plurality of optically conducting fibres 411 can be fixed to the electrically conducting core 410 in any suitable way, for example using a suitable adhesive.

The distal end 412 of the optode arrangement 409 is configured to contact the surface of a subject's head. As can be seen, the electrically conducting core 410 and the plurality of optically conducting fibres 411 terminate at substantially the same point along the axis of the optode arrangement 409 thus ensuring that the electrically conducting core 410 and optically conducting fibres 411 will be brought into contact with the surface of the subject's head at same time, and to the same degree, when the optode arrangement 409 is positioned on the subject's head.

In keeping with the embodiment described with reference to FIG. 4a, the proximal end of the optode arrangement 413 can be configured in any suitable way enabling the electrically conducting core 408 to be connected to the impedance measuring unit and the optically conducting fibres 411 to be connected to the NIR transmitter or receiver unit.

In the example depicted in FIG. 4b, the proximal end of the optode arrangement 409 is configured so that the electrically conducting core 410 extends 414 beyond the terminating ends of the optically conducting fibres 411 so that it can readily be connected to the impedance measuring unit by a suitable electrical connection. The terminating ends of the optically conducting fibres 411 may be connected to a suitable optical element (for example an annular lens) configured to direct NIR radiation from a NIR transmitter unit or to a NIR receiver unit.

FIG. 7 provides a schematic diagram depicting a near-infrared imaging system 701 for identifying a target feature in an object in accordance with certain embodiments of the invention. The system 701 substantially corresponds with the system of FIG. 1 except as otherwise described and depicted.

The system 701 includes a transmitter receiver array comprising a plurality of NIR radiation generators 702 and a plurality of NIR radiation detectors 703 coupled to NIR radiation transmit/receive unit 704 (provided, for example in a headset). It will be understood that in certain embodiments, components of the transmitter receiver array can operate as both NIR radiation generators and NIR radiation detectors by selectively operating in a transmit or receive mode of operation.

In contrast with the system of FIG. 1, the NIR radiation generating 702 and NIR radiation detecting 703 components of the system 701 make direct contact with the subject's head. In this way, the NIR radiation is directly transmitted and received without being directed through separate optode components.

Operation of the NIR radiation transmit/receive unit 704 and in particular the NIR radiation generators 702 and NIR radiation detectors 703 is controlled by a control unit 705, typically provided by a suitably programmed computing device including a memory and processor.

Output signals detected by the NIR radiation detectors 703 are communicated via a suitable signal line to a data processing system 706, typically provided by a suitable programmed computer.

The system 701 also includes further signal transmitting and signal receiving means 707, 708. The further signal transmitting and receiving means 707, 708 are configured to respectively transmit and receive further signals. The further signals can be transmitted via components associated with the transmitter receiver array that make contact with the subject's head. The further signals are typically ultrasound or electrical signals.

Data relating to these received further signals is then communicated to the data processing system 706 and used to generate model constraints to modify the near-infrared spectroscopy imaging model to take account of variations in various factors such as the way that the transmitter receiver array is engaged with the subject's head.

Figure 8:
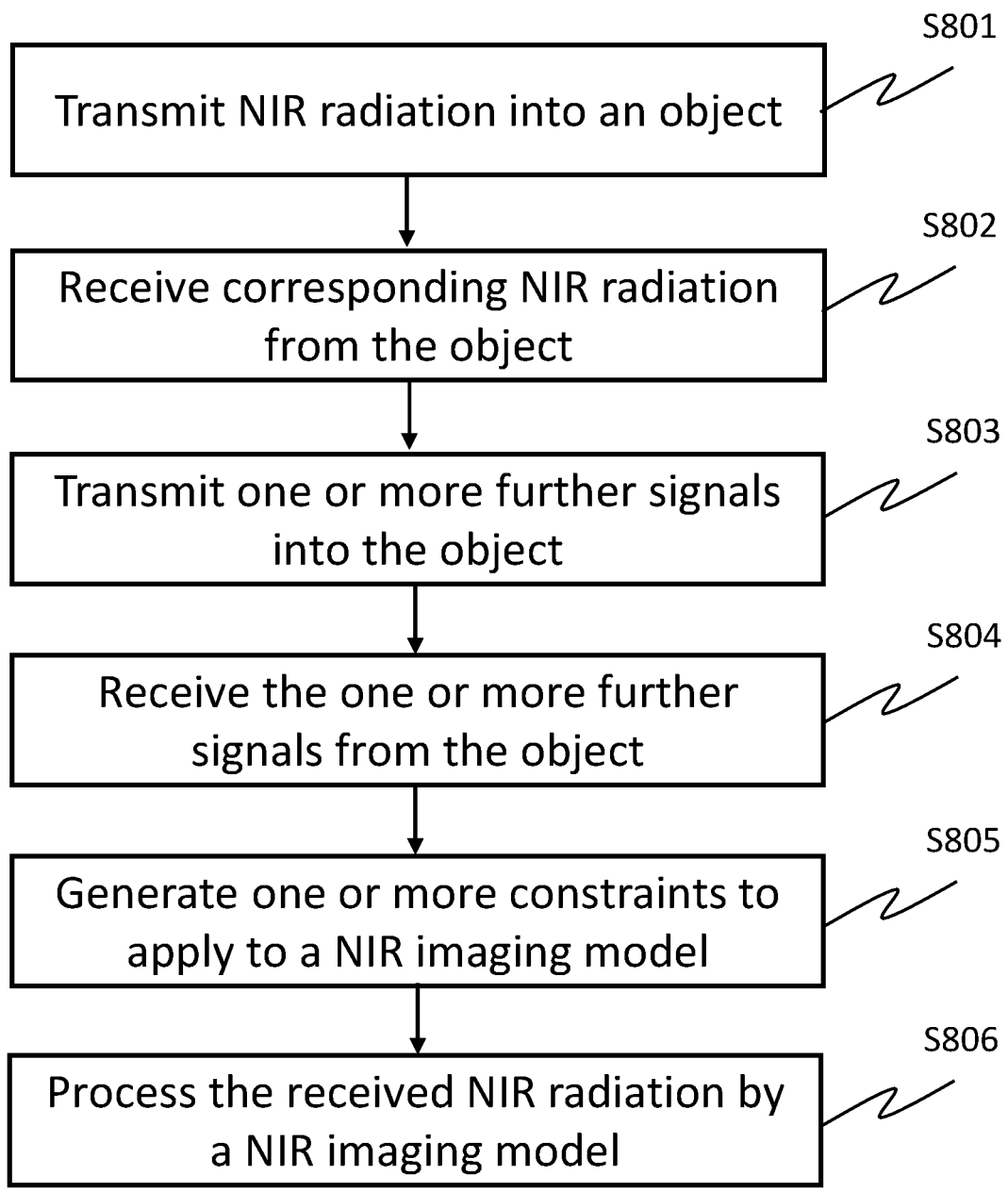
FIG. 8 provides a simplified flow diagram depicting a method of generating one or more constraints to apply to a near-infrared imaging model in accordance with certain embodiments of the invention.

FIG. 8 provides a flow diagram of a method of generating one or more constraints to apply to a near-infrared imaging model in accordance with embodiments of the invention.

The method is typically implemented on a near-infrared imaging system of a type described herein in accordance with embodiments of the invention. It will be understood that the method can include further features and steps described herein with reference to such systems.

At step S801, near-infrared radiation is transmitted via a near-infrared transmitter receiver array into an object. In certain embodiments, the object is a subject's head.

At step S802, corresponding near-infrared radiation emitted from the object is received via the near-infrared transmitter receiver array. Steps S801 and S802 are typically performed by NIR radiation generators and detectors operating under the control of a control unit.

At step S803, one or more further signals are transmitted into the object. Such further signals can be ultrasound or electrical signals.

At step S804, the one more further signals are received from the object.

At step S805, one or more characteristics of the received one or more further signals are processed to generate one or more constraints to apply to the near-infrared imaging model. Typically, such processing is performed by the data processing system.

At step S806, the one or more constraints are applied to the near-infrared imaging model and near-infrared radiation received via the near-infrared transmitter receiver array is processed in accordance with the near-infrared imaging model to identify the presence or absence of a target feature within the object. Typically, such processing is performed by a data processing system.

Optodes have been described herein as receive optodes or transmit optodes. It will be understood however that in certain embodiments, a single optode can operate as both a transmit optode and a receive optode. Such a transmit/receive optode can be connected to a NIR radiation generator unit and a NIR radiation detector unit and can operate in a transmit mode or a receive mode.

Embodiments of the invention have been described in the context of imaging a human subject's head. It will be understood, however, that in other embodiments, the system can be used, with suitable modification, for imaging other parts of the human body.

For example, in certain embodiments, the system can be used for imaging a human subject's foot, chest or other suitable region of the subject's body. It will be understood that in certain embodiments, the system can be used, with suitable modification, for imaging parts of a non-human animal.

Embodiments of the invention have been described in the context of near-infrared spectroscopy. It will be understood, however, that techniques disclosed herein can be applied, with suitable modification, to other near-infrared imaging techniques such as near-infrared tomography.

Although in the examples described above, systems have been described that generate constraints by using ultrasound signals or by using electrical signals, the skilled person would understand that in other embodiments, a system can generate constraints by using a combination of ultrasound signals and electrical signals.

All of the features disclosed in this specification (including any accompanying claims, abstract and drawings), and/or all of the steps of any method or process so disclosed, may be combined in any combination, except combinations where at least some of such features and/or steps are mutually exclusive. Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

It will be appreciated that various embodiments of the present disclosure have been described herein for purposes of illustration, and that various modifications may be made without departing from the scope of the present disclosure. Accordingly, the various embodiments disclosed herein are not intended to be limiting, with the true scope being indicated by the following claims.

The invention claimed is:

1. A near-infrared imaging system for identifying a target feature in an object, said system comprising:
   a near-infrared transmitter receiver array for transmitting near-infrared radiation into the object and receiving corresponding near-infrared radiation emitted from the object, wherein the near-infrared transmitter receiver array is an optode array comprising a plurality of optodes each having a distal end arranged to make contact with a surface of the object; and
   a data processing system configured to process near-infrared radiation received via the near-infrared transmitter receiver array in accordance with a near-infrared imaging model to identify the presence or absence of the target feature within the object, wherein the system further comprises:
   signal transmitting means arranged to transmit one or more further signals into the object via one or more optodes of the optode array, wherein the one or more further signals comprise ultrasound signals and/or electrical signals; and
   signal receiving means arranged to receive the one or more further signals from the object via one or more optodes of the optode array, and wherein
   the data processing system is further configured to process one or more characteristics of the one or more further signals received by the signal receiving means to determine a material composition of the object between a contact point of an optode via which the signal was transmitted and a contact point of an optode via which the signal was received, and to generate one or more corresponding constraints to apply to the near-infrared imaging model.

2. A near-infrared imaging system according to claim 1, wherein the signal transmitting and signal receiving means comprise one or more ultrasound transducers and the one or more further signals comprise ultrasound signals.

3. A near-infrared imaging system according to claim 1, wherein the data processing system is configured to process one or more characteristics of the received one or more further signals to determine a level of contact between one or more optodes of the optode array and the surface of the object, and to generate one or more corresponding constraints to apply to the near-infrared imaging model.

4. A near-infrared imaging system according to claim 1, wherein the data processing system is configured to process one or more characteristics of the received one or more further signals to determine a distance of a contact point of an optode via which the signal was transmitted from a contact point of an optode via which the signal was received, and to generate one or more corresponding constraints to apply to the near-infrared imaging model.

5. A near-infrared imaging system according to claim 1, wherein the data processing system is configured to process one or more characteristics of the received one or more further signals to determine a distance of a contact point of an optode via which the signal was transmitted from a plurality of contact points of optodes via which the signal was received, and to generate one or more corresponding constraints to apply to the near-infrared imaging model.

6. A near-infrared imaging system according to claim 1, wherein the data processing system is configured to process one or more characteristics of the received one or more further signals to determine a thickness of an outermost layer or layers of the object, and to generate one or more corresponding constraints to apply to the near-infrared imaging model.

7. A near-infrared imaging system according to claim 2, wherein the signal transmitting means is arranged to transmit one or more still further signals into the object, the still further signals comprising acoustic signals that cause periodic compression of a region of the object.

8. A near-infrared imaging system according to claim 7, wherein the acoustic signals have a frequency of between 10 Hz and 100 kHz.

9. A near-infrared imaging system according to claim 7, wherein the data processing system is configured to process near-infrared radiation received via the near-infrared transmitter receiver array to identify an amount of modulation present in the received near-infrared radiation caused by the periodic compression of the region of the object, and to generate one or more corresponding constraints to apply to the near-infrared imaging model.

10. A near-infrared imaging system according to claim 1, wherein the signal transmitting and signal receiving means comprise one or more impedance measuring devices and the one or more signals comprise electrical signals.

11. A near-infrared imaging system according to claim 10, wherein the electrical signals are transmitted and received via one or more electrodes associated with optodes of the array.

12. A near-infrared imaging system according to claim 11, wherein the one or more electrodes are each coupled to the optode with which they are associated.

13. A near-infrared imaging system according to claim 12, wherein each of the one or more electrodes is formed by an electrically conducting layer surrounding an optically transmissive core which forms the optode with which the electrode is associated.

14. A near-infrared imaging system according to claim 13, further comprising an insulating layer surrounding each electrically conducting layer.

15. A near-infrared imaging system according to claim 12, wherein each electrode is formed by an electrically conducting core surrounded by an optically conducting outer layer that forms the optode with which the electrically conducting core is associated.

16. A near-infrared imaging system according to claim 15, wherein the optically conducting outer layer substantially insulates the electrically conducting core.

17. A near-infrared imaging system according to claim 16, wherein the optically conducting outer layer comprises a plurality of optode fibres.

18. A near-infrared imaging system according to claim 1, wherein the data processing system is configured to perform a demodulation process on detected near-infrared radiation prior to processing the detected near-infrared radiation in accordance with the near-infrared imaging model.

19. A near-infrared imaging system according to claim 1, wherein the target feature is a change in perfusion or liquid content of biological tissue.

20. A near-infrared imaging system according to claim 1, wherein the target feature is indicative of a target pathology.

21. A near-infrared imaging system according to claim 20, wherein the target pathology is an intracranial haematoma, intracranial haemorrhage, or change in blood flow, blood oxygenation or blood volume characteristic of cerebral ischaemia.

22. A near-infrared imaging system according to claim 1, wherein the object is a subject's head.

23. A near-infrared imaging system according to claim 1, wherein the object is a subject's foot or chest.

24. A near-infrared imaging system according to claim 1, wherein the system is a near-infrared spectroscopy or near-infrared tomography system.

25. A method of generating one or more constraints to apply to a near-infrared imaging model, the method comprising:
   transmitting, via a near-infrared transmitter receiver array, near-infrared radiation into an object;
   receiving, via the near-infrared transmitter receiver array, corresponding near-infrared radiation emitted from the object, wherein the near-infrared transmitter receiver array is an optode array comprising a plurality of optodes each having a distal end arranged to make contact with a surface of the object;
   transmitting one or more further signals into the object via one or more optodes of the optode array, wherein the one or more further signals comprise ultrasound signals and/or electrical signals;
   receiving the one more further signals from the object via one or more optodes of the optode array;
   processing one or more characteristics of the received one or more further signals to determine a material composition of the object between a contact point of an optode via which the signal was transmitted and a contact point of an optode via which the signal was received, and to generate one or more corresponding constraints to apply to the near-infrared imaging model;
   applying the one or more constraints to the near-infrared imaging model; and
   processing near-infrared radiation received via the near-infrared transmitter receiver array in accordance with the near-infrared imaging model to identify the presence or absence of a target feature within the object.

* * * * *